(12) United States Patent
Traynelis et al.

(10) Patent No.: US 9,314,345 B2
(45) Date of Patent: Apr. 19, 2016

(54) SPINAL IMPLANT SYSTEM AND METHOD

(76) Inventors: Vincent Traynelis, Chicago, IL (US);
Trevor T. Seck, Memphis, TN (US);
Gregory C. Marik, Collierville, TN (US)

(*) Notice: Subject to any disclaimer, the term of this patent is extended or adjusted under 35 U.S.C. 154(b) by 645 days.

(21) Appl. No.: 13/547,631

(22) Filed: Jul. 12, 2012

(65) Prior Publication Data

US 2014/0018869 A1    Jan. 16, 2014

(51) Int. Cl.
| A61F 2/46 | (2006.01) |
| A61F 2/44 | (2006.01) |
| A61F 2/30 | (2006.01) |
| A61F 2/28 | (2006.01) |

(52) U.S. Cl.
CPC .............. *A61F 2/44* (2013.01); *A61F 2/4611* (2013.01); *A61F 2/442* (2013.01); *A61F 2/4405* (2013.01); *A61F 2/4455* (2013.01); *A61F 2002/2817* (2013.01); *A61F 2002/2835* (2013.01); *A61F 2002/3008* (2013.01); *A61F 2002/30082* (2013.01); *A61F 2002/3093* (2013.01); *A61F 2002/30616* (2013.01); *A61F 2002/30677* (2013.01); *A61F 2002/30772* (2013.01); *A61F 2002/4681* (2013.01); *A61F 2002/4685* (2013.01); *A61F 2310/00023* (2013.01); *A61F 2310/00131* (2013.01); *A61F 2310/00293* (2013.01); *A61F 2310/00359* (2013.01)

(58) Field of Classification Search
CPC ......... A61F 2/44; A61F 2/4611; A61F 2/442; A61F 2/4455
See application file for complete search history.

(56) References Cited

U.S. PATENT DOCUMENTS

| 3,724,076 | A |  | 4/1973 | Schmitz |
| 3,859,992 | A | * | 1/1975 | Amstutz ........................ 606/91 |
| 3,963,028 | A |  | 6/1976 | Cooley et al. |
| 4,769,011 | A |  | 9/1988 | Swaniger |
| 5,336,170 | A |  | 8/1994 | Salerno et al. |
| 6,048,346 | A |  | 4/2000 | Reilley et al. |
| 6,270,502 | B1 |  | 8/2001 | Stulberg |
| 7,066,942 | B2 |  | 6/2006 | Treace |
| 7,160,306 | B2 |  | 1/2007 | Matsuzaki |
| 7,226,413 | B2 |  | 6/2007 | McKinley |
| 7,802,574 | B2 |  | 9/2010 | Schultz |
| 7,819,880 | B2 |  | 10/2010 | Zannis et al. |
| 8,012,141 | B2 |  | 9/2011 | Wright et al. |
| 2003/0225456 | A1 | * | 12/2003 | Ek .............................. 623/20.14 |
| 2007/0093903 | A1 | * | 4/2007 | Cheng ........................ 623/17.12 |
| 2007/0244493 | A1 |  | 10/2007 | Bjerken |
| 2008/0071281 | A1 | * | 3/2008 | Wilson et al. ................... 606/92 |
| 2011/0264098 | A1 |  | 10/2011 | Cobbs |

* cited by examiner

*Primary Examiner* — Andrew Yang

(57) ABSTRACT

A surgical instrument comprises a first wall defining a cavity disposed for communication with a suction source and extending between a first end and a second end. The first end includes at least a portion of a valve disposed for communication with the cavity. The second end includes at least a portion of an implant engaging surface. A second wall is connected to the first wall and extending between a first end and a second end. The first end includes an impact surface and the second end includes at least a portion of the implant engaging surface. Methods of use are disclosed.

20 Claims, 6 Drawing Sheets

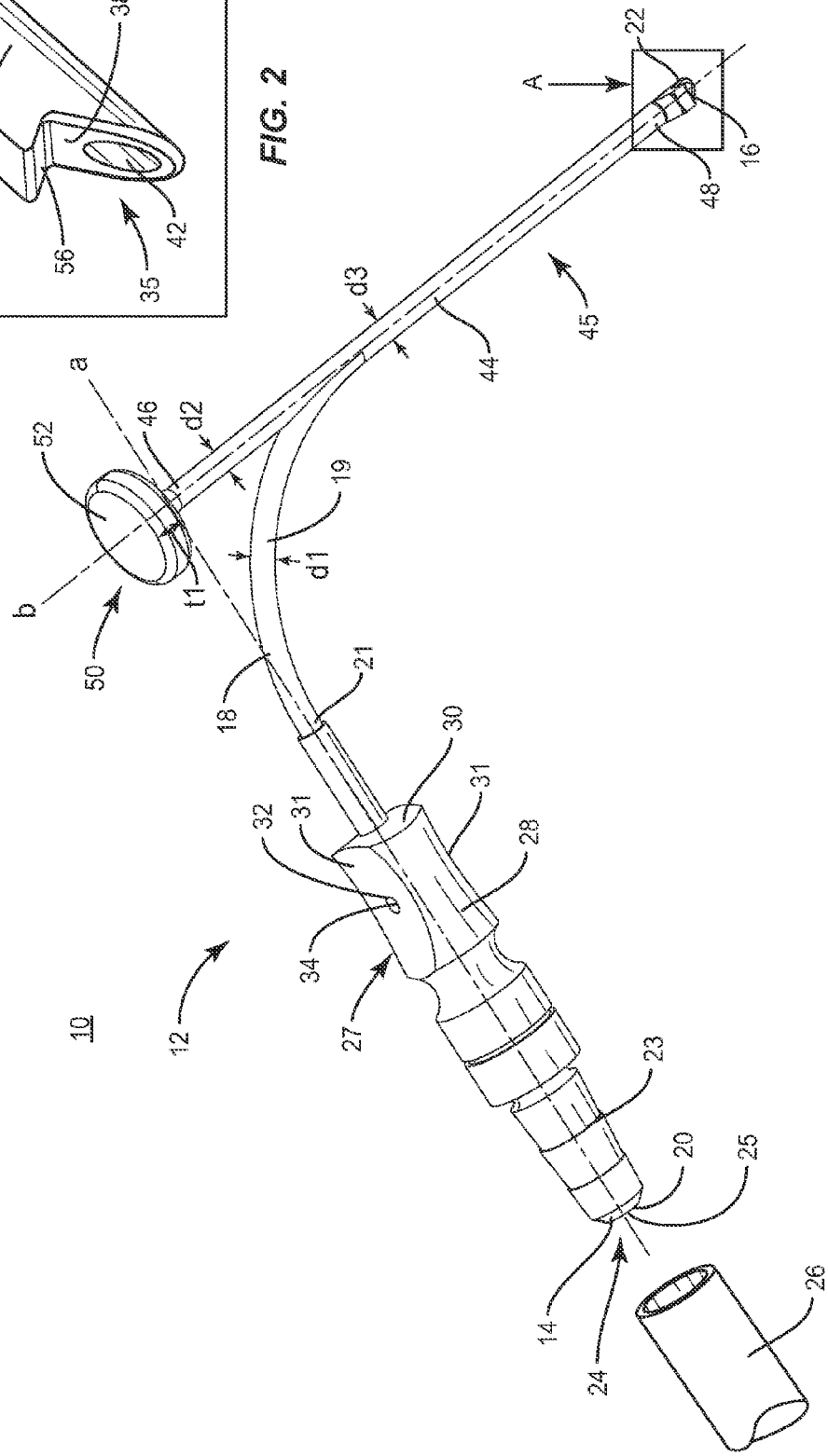

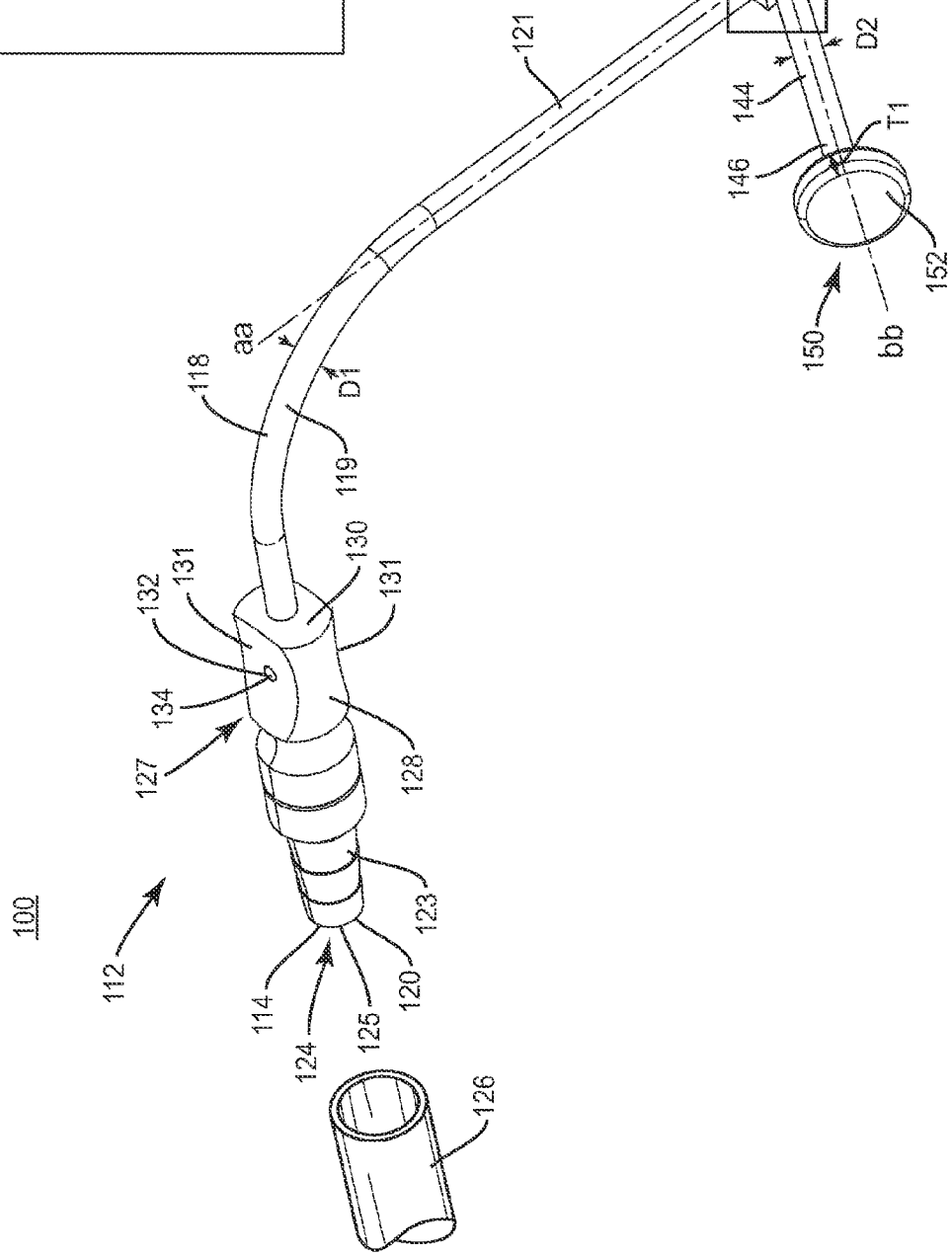

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

In one embodiment, in accordance with the principles of the present disclosure, an implant delivery device is provided. The device comprises a first wall defining a cavity disposed for communication with a suction source. The first wall extends between a first end and a second end. The first end includes at least a portion of a valve disposed for communication with the cavity. The second end includes at least a portion of an implant engaging surface. A second wall is connected to the first wall. The second wall extends between a first end and a second end. The first end includes an impact surface and the second end includes at least a portion of the implant engaging surface.

In one embodiment, an implant delivery system is provided. The system comprises a tubular conduit that includes an inner surface defining a first passageway. The conduit extends between a first end and a second end. The first end includes at least a portion of a valve that includes a valve body having an outer surface. The outer surface includes a concave surface defining a centrally disposed opening. The opening includes a second passageway that is disposed in communication with the first passageway. The second end includes at least a portion of an end surface that defines a distal opening. The system includes a suction source that communicates with the first passageway. An impact shaft is provided that defines a longitudinal axis and is connected with the conduit such that the conduit extends transversely therefrom. The shaft includes a first end having a circular configuration defining a thickness and including a planar impact surface. The shaft includes a second end including at least a portion of the end surface defining an implant face. The opening of the valve body is disposed for engagement with a valve part that is configured to close the second passageway such that the suction source draws a fluid through the first passageway to draw an implant into engagement with the distal opening and the valve part is disengageable from the opening to open the second passageway such that the implant is released from the distal opening.

In one embodiment, in accordance with the principles of the present disclosure, a method for delivering an implant to a surgical site is provided. The method comprises the steps of: providing an implant delivery device comprising a first wall defining a cavity disposed for communication with a suction source and extending between a first end and a second end, the first end including at least a portion of a valve disposed for communication with the cavity, the second end including at least a portion of an implant engaging surface, and a second wall connected to the first wall and extending between a first end and a second end, the first end including an impact surface and the second end including at least a portion of the implant engaging surface; providing an implant; engaging the valve to close the cavity; applying suction to the cavity to draw fluid through the cavity such that the implant is drawn into engagement with the implant engaging surface; delivering the implant to the surgical site; engaging the impact surface such that the implant engaging surface selectively positions the implant at the surgical site; and disengaging the valve to release the implant from the implant engaging surface at the surgical site.

BRIEF DESCRIPTION OF THE DRAWINGS

The present disclosure will become more readily apparent from the specific description accompanied by the following drawings, in which:

FIG. 1 is a perspective view of one particular embodiment of a system in accordance with the principles of the present disclosure;

FIG. 2 is an enlarged perspective view of detail A shown in FIG. 1;

FIG. 7 is a perspective view of one embodiment of a system in accordance with the principles of the present disclosure; and FIG. 8 is an enlarged perspective view of detail B shown in FIG. 7.

Like reference numerals indicate similar parts throughout the figures.

DETAILED DESCRIPTION

Figure 3:
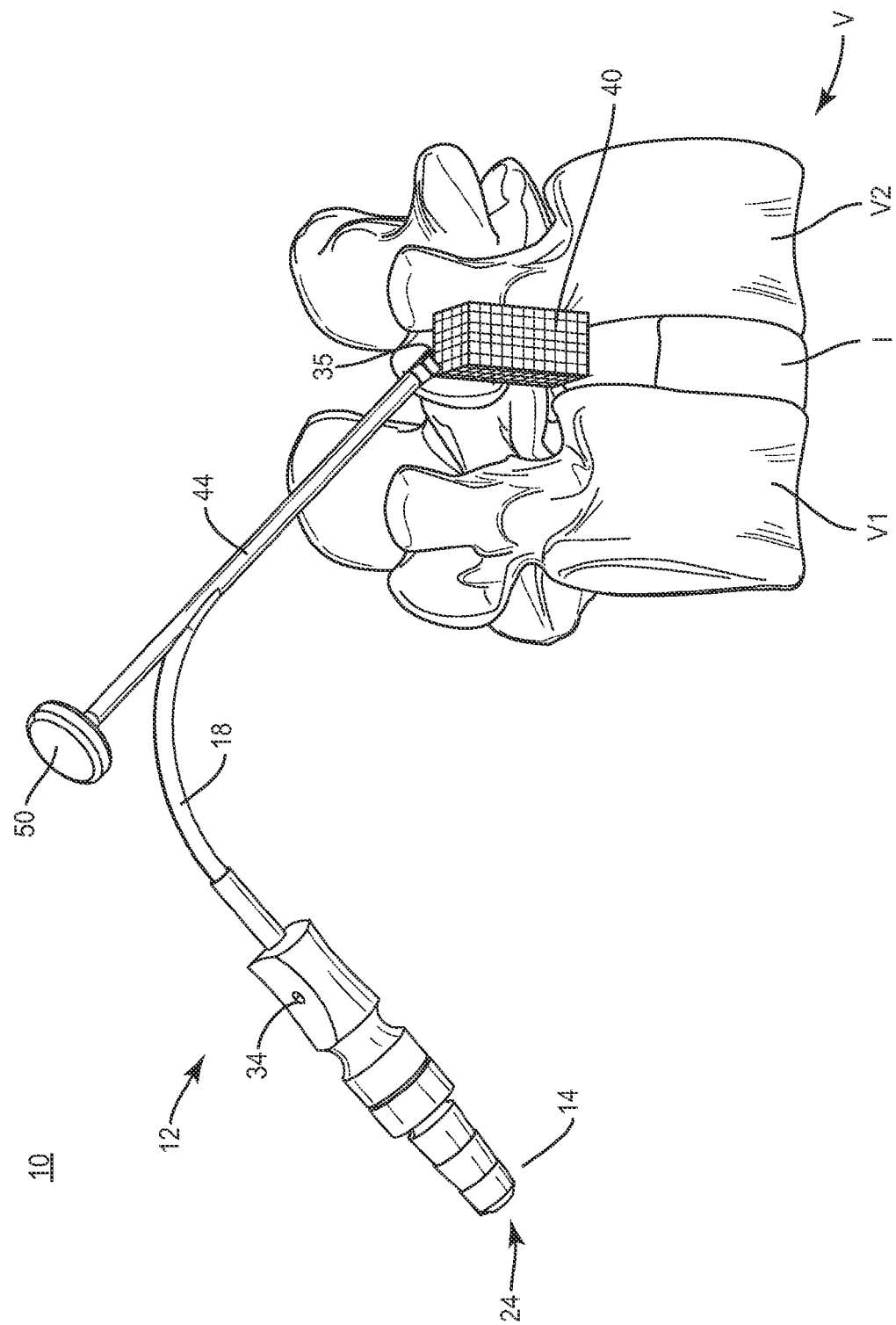
FIG. 3 is a perspective view of one embodiment of a system in accordance with the principles of the present disclosure disposed with vertebrae.
Figure 4:
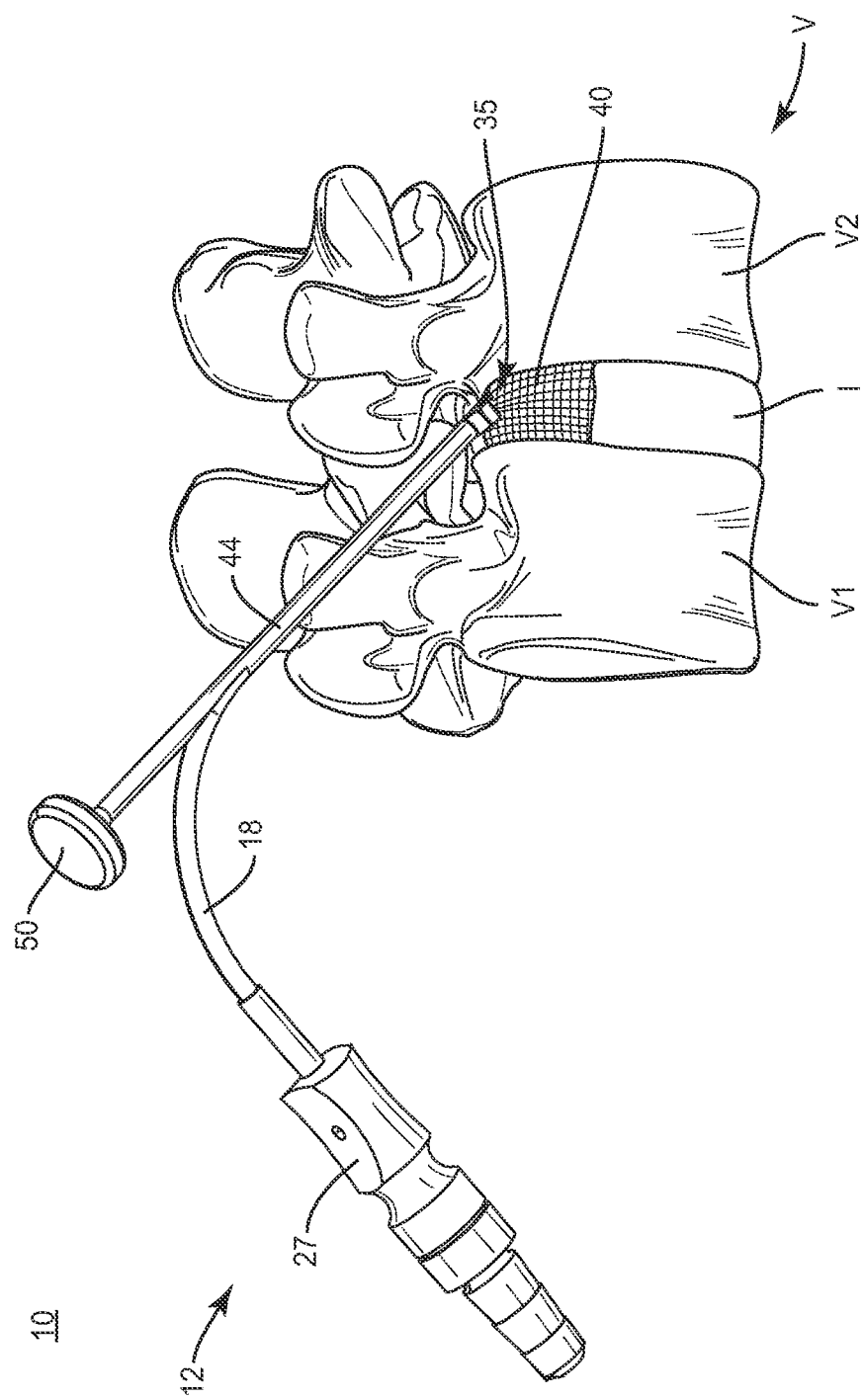
FIG. 4 is a perspective view of the system and vertebrae shown in FIG. 3.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical system and method of use disclosed provide reliable and safe access to a spinal region to deliver an implant. It is further envisioned that the surgical system is configured to deliver an implant to a spinal region for an arthrodesis treatment, such as, for example, fusion and fixation.

In one embodiment, the system includes instruments that are connected or attached to a suction facet graft holder. It is contemplated that the system can include a suction graft holder having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In one embodiment, the system includes a suction graft holder comprising a suction control that includes a pressure valve. In one embodiment, the holder includes an impaction end to apply force to an implant. In one embodiment, the holder includes a graft placement portion defined by two portions disposed in an angular orientation. In one embodiment, the two portions are disposed in a perpendicular orientation.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-2, there is illustrated components of a surgical system, such as, for example, a spinal implant delivery system 10 in accordance with the principles of the present disclosure.

The components of spinal implant delivery system 10 can be fabricated from biologically acceptable materials suitable for medical applications, including metals, synthetic polymers, ceramics and bone material and/or their composites, depending on the particular application and/or preference of a medical practitioner. For example, the components of spinal implant delivery system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant delivery system 10 may have material composites, including the above materials, to achieve various desired characteristics such as strength, rigidity, elasticity, compliance, biomechanical performance, durability and radiolucency or imaging preference. The components of spinal implant delivery system 10, individually or collectively, may also be fabricated from a heterogeneous material such as a combination of two or more of the above-described materials. The components of spinal implant delivery system 10 may be monolithically formed, integrally connected or include fastening elements and/or instruments, as described herein.

Spinal implant delivery system 10 is employed, for example, with a minimally invasive procedure, including percutaneous techniques, mini-open and open surgical techniques to deliver and introduce an implant, which may include, for example, bone graft, at a surgical site within a body of a patient, for example, a section of a spine.

Spinal implant delivery system 10 includes an implant delivery device 12. Device 12 is configured for engagement with an implant and a suction source, to deliver the implant to a surgical site, as described herein. Device 12 extends between a proximal end 14 and a distal end 16. Device 12 includes a first wall, such as, for example, a tubular conduit 18. Conduit 18 extends between a first end 20 and a second end 22. Conduit 18 defines a cavity 24 that extends between ends 20, 22. Conduit 18 includes an opening 25 at end 20. Opening 25 is disposed in communication with cavity 24.

Conduit 18 is configured to draw a fluid, via connection to the suction source, through cavity 24, as described herein. It is envisioned that the fluid may include a gas, liquid or solid and/or mixtures and combinations thereof. For example, the gas may include air and/or oxygen supplied and/or delivered to a surgical site and drawn through conduit 18. For example, the liquid may include sterile water, saline, mineral compositions, polymers and/or curable materials supplied and/or delivered to a surgical site and drawn through conduit 18. For example, the solid may include a powder supplied and/or delivered to a surgical site and drawn through conduit 18. In one embodiment, the fluid includes a mixture of a gas such as air and an initially flowable material that changes from a liquid to a relatively solid non-flowable form having a significantly higher modulus of elasticity relative to the initial fluid form that molds in situ with an implant.

Conduit 18 includes a linear portion 21 defining an axis a extending from end 20. Conduit 18 has an arcuate portion 19, which has a diameter d1 and extends from portion 21. Diameter d1 is uniform. It is contemplated that conduit 18 may have various cross-section configurations, such as, for example, oval, rectangular, polygonal, irregular, tapered, offset, staggered, uniform and non-uniform. It is envisioned that one or all of the surfaces of conduit 18 may have alternate surface configurations, such as, for example, rough, threaded for connection with surgical instruments, arcuate, undulating, porous, semi-porous, dimpled, polished and/or textured according to the requirements of a particular application.

A suction source 26 is attached to end 20 of conduit 18. Source 26 includes flexible tubing and/or a cannulated instrument configured to draw fluid therethrough. The tubing is releasably connected to end 20. End 20 includes a luer connector port 23 adapted for a sealed connection with the tubing of source 26. It is envisioned that end 20 may be releasably connected, attached or monolithically formed with source 26. It is further envisioned that port 23 may alternatively include a threaded connection or quick disconnect coupling.

Source 26 is a source of vacuum configured to draw the fluid through cavity 24, as described herein. Source 26 includes a pump or other gas exhausting device to create vacuum. It is contemplated that source 26 can be hydraulic or pneumatic.

End 20 includes a valve 27. Valve 27 is configured to selectively regulate the amount of fluid suction flowing through conduit 18 along cavity 24. Valve 27 includes a valve body 28. Body 28 includes an outer surface 30. Surface 30 defines a centrally disposed opening 32. Opening 32 communicates with a passageway 34 disposed in communication with cavity 24. Surface 30 includes concave portions 31, disposed on sides of body 28 and oriented in opposing directions, configured for engagement with a valve part (not shown). The valve part is engageable with portions 31 to selectively regulate suction and the drawing of fluid through conduit 18. Portions 31 are configured to receive the valve part, such as, for example, finger surface(s) of a medical practitioner. The finger surface(s) engage opening 32 to close and/or seal passageway 34 to enable the vacuum such that suction is provided to cavity 24 for drawing fluid through conduit 18. The finger surface(s) disengage from opening 32 to disable vacuum such that suction is relieved from cavity 24 and fluid is not drawn through conduit 18. In one embodiment, body 28 has a single opening 32. In one embodiment, portions 31 are planar. It is envisioned that the valve part may alternatively be a mechanical plug, hinge plug, tethered plug, dial regulated blockage and/or motorized valve component.

End 16 includes an implant engaging surface 35. It is contemplated that all or a portion of surface 35 may have alternate surface configurations according to the requirements of a particular application. Surface 35 includes a face 38, as shown in FIG. 2. Face 38 is configured for engagement with an implant 40 (FIG. 3) and defines an opening 42. Opening 42 communicates with cavity 24 and is configured to provide a fluid and/or suction to draw implant 40 into engagement with surface 35, as described herein. It is contemplated that opening 42 may be configured in various shapes depending upon, for example, the size and shape of cavity 24, the region of the spine in which an implant is inserted between and/or the type of material placed therein.

Conduit 18 is connected with a second wall, such as, for example, an impact shaft 44. Shaft 44 extends between a first end 46 and a second end 48. Shaft 44 defines a longitudinal axis b extending between ends 46, 48. Conduit 18 extends transversely from axis b. In one embodiment, conduit 18 extends from shaft 44 at a 45-degree angle relative to axis b. In one embodiment, conduit 18 extends from shaft 44 at a 90-degree angle relative to axis b. Shaft 44 connects to conduit 18 via an outer surface of conduit 18 and is not in communication with cavity 24.

Shaft 44 has a solid configuration and has a diameter d2. Diameter d2 is uniform. It is contemplated that shaft 44 may have various cross-section configurations, for example, oval, rectangular, polygonal, irregular, tapered, offset, staggered, uniform and non-uniform. It is envisioned that one or all of the surfaces of shaft 44 may have alternate surface configurations, such as, for example, rough, threaded for connection with surgical instruments, arcuate, undulating, porous, semi-porous, dimpled, polished and/or textured according to the requirements of a particular application. Shaft 44 merges with conduit 18 via portion 19 to define a merged portion 45 having a third diameter portion d3. Diameter d3 is uniform. It is envisioned that d3 is greater than d1 and d2. Merged portion 45 includes conduit 18 and solid shaft 44 such that cavity 24 extends uniformly therethrough.

End 46 includes an impact surface 50. Surface 50 is circular. It is contemplated that surface 50 may be alternately configured, such as, for example, arcuate, pointed, round, square, rectangular, polygonal or oval. It is contemplated that surface 50 may be smooth, rough, polished or textured according to the requirements of a particular application. Surface 50 includes a planar face 52. Face 52 is configured for engagement with a medical instrument, such as, for example, a mallet, hammer or impactor. Surface 50 has a thickness, such as, for example, thickness t1. It is contemplated that the thickness of surface 50 may vary according to the requirements of a particular application.

End 48 includes an impact face 56, which comprises a portion of implant engaging surface 35, as shown in FIG. 2. Face 56 is disposed at an angular orientation relative to face 38. Face 56 is configured for engagement with implant 40 and assists in the delivery and positioning of implant 40 at a surgical site, as described herein. In one embodiment, face 56 is disposed in a perpendicular orientation relative to face 38. It is envisioned that face 56 may be disposed in a range of angular orientations relative to face 38, for example, in a range of 15-345 degrees. It is contemplated that face 56 may be rough, arcuate, undulating, porous, semi-porous, dimpled, polished and/or textured according to the requirements of a particular application.

In operation, spinal implant delivery system 10, similar to that described above, is used to deliver implant 40 to a surgical site. It is envisioned that spinal implant delivery system 10 may be used in any existing surgical method or technique including open surgery, mini-open surgery, minimally invasive surgery and percutaneous surgical implantation. Spinal implant delivery system 10 may also be employed with other surgical procedures. For example, spinal implant delivery system 10 can be used with a surgical procedure for treatment of a condition or injury of an affected section of the spine including vertebrae V. In use, to treat the affected section of vertebrae V, a medical practitioner obtains access to a surgical site including vertebrae V1, V2 and an intervertebral disc space I in any appropriate manner. For example, during the surgical procedure, a surgeon will make an incision in the skin of a patient. In one embodiment, a dilator may be employed to separate the muscles and tissues to create a passageway and/or sleeve through which the surgery may be performed.

In one embodiment, a retractor is positioned and docked adjacent the surgical site over the incision. The passageway is created and extends from the incision to approximately adjacent the surgical site. A cutting instrument is inserted within the passageway and creates a bore in the surgical site. It is envisioned that the cutting instrument may include a drill, trephine or reamer. The cutting instrument is removed from the passageway thereafter.

A preparation instrument(s) is inserted within the passageway and disposed within the surgical site. It is envisioned that the preparation instrument(s) may include rasps, curettes and/or a rotating tissue remover such as a rapid disc removal system that can be low profile to cut and remove discs and/or bone material simultaneously. The preparation instrument(s) is employed to remove disc tissue and fluids, adjacent tissues and/or bone, scrape and/or remove tissue from endplate surfaces, as well as for aspiration and irrigation of the region according to the requirements of a particular surgical application. The preparation instrument is removed from the passageway thereafter.

Implant 40 is positioned at end 16 to engage surface 35 of delivery device 12. Suction source 26 is connected to end 20, as described, to enable vacuum for drawing fluid through conduit 18. Concave portions 31 of surface 30 are engaged with finger surface(s) of a medical practitioner, to seal cavity 24 to enable vacuum and to create suction through cavity 24. Fluid is drawn through conduit 18 such that suction flows through cavity 24 extending to opening 42. The fluid suction draws implant 40 into engagement with surface 35 so that implant 40 is releasably fixed with surface 35, as shown in FIG. 3. With implant 40 fixed with surface 35, device 12 is introduced to the surgical site via the passageway to deliver implant 40 to the surgical site.

Upon delivery of implant 40 to the surgical site, implant 40 maintains engagement with surface 35. A force is applied to impact surface 50 via a surgical mallet, which translates along shaft 44 to impact face 56. Impact face 56 engages and applies the force to implant 40 to position implant 40 within intervertebral disc space I, according to the requirements of a particular application.

The finger surface(s) are disengaged from opening 32 so that passageway 34 opens cavity 24. Vacuum is disabled such that suction is relieved from cavity 24, as described. Implant 40 is released from surface 35 and implant 40 is implanted with intervertebral disc space I. Once implant 40 is released, device 12 is removed from the surgical site and the incision is closed.

It is envisioned that spinal implant delivery system 10 may be completely or partially revised, removed or replaced, for example, removing conduit 18 and/or shaft 44, suction 26, implant 40 and/or one or all of the components of the spinal implant system during or after the surgical procedure.

It is envisioned that implant 40 may include one or a plurality of a cage, spinal rod, connector and/or a bone fastener. It is further envisioned that implant 40 may be variously configured including cylindrical, rectangular, oval, uniform, non-uniform, mesh, staggered and/or undulating. In one embodiment, implant 40 includes an agent, which may be disposed, packed or layered within, on or about the surfaces of implant 40. It is envisioned that the agent may include bone growth promoting material, such as, for example, bone graft to enhance fixation of the fixation elements with vertebrae V.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Implant 40 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration. Metallic or ceramic radiomarkers, such as tantalum beads, tantalum pins, titanium pins, titanium endcaps and platinum wires can be used.

Figure 5:
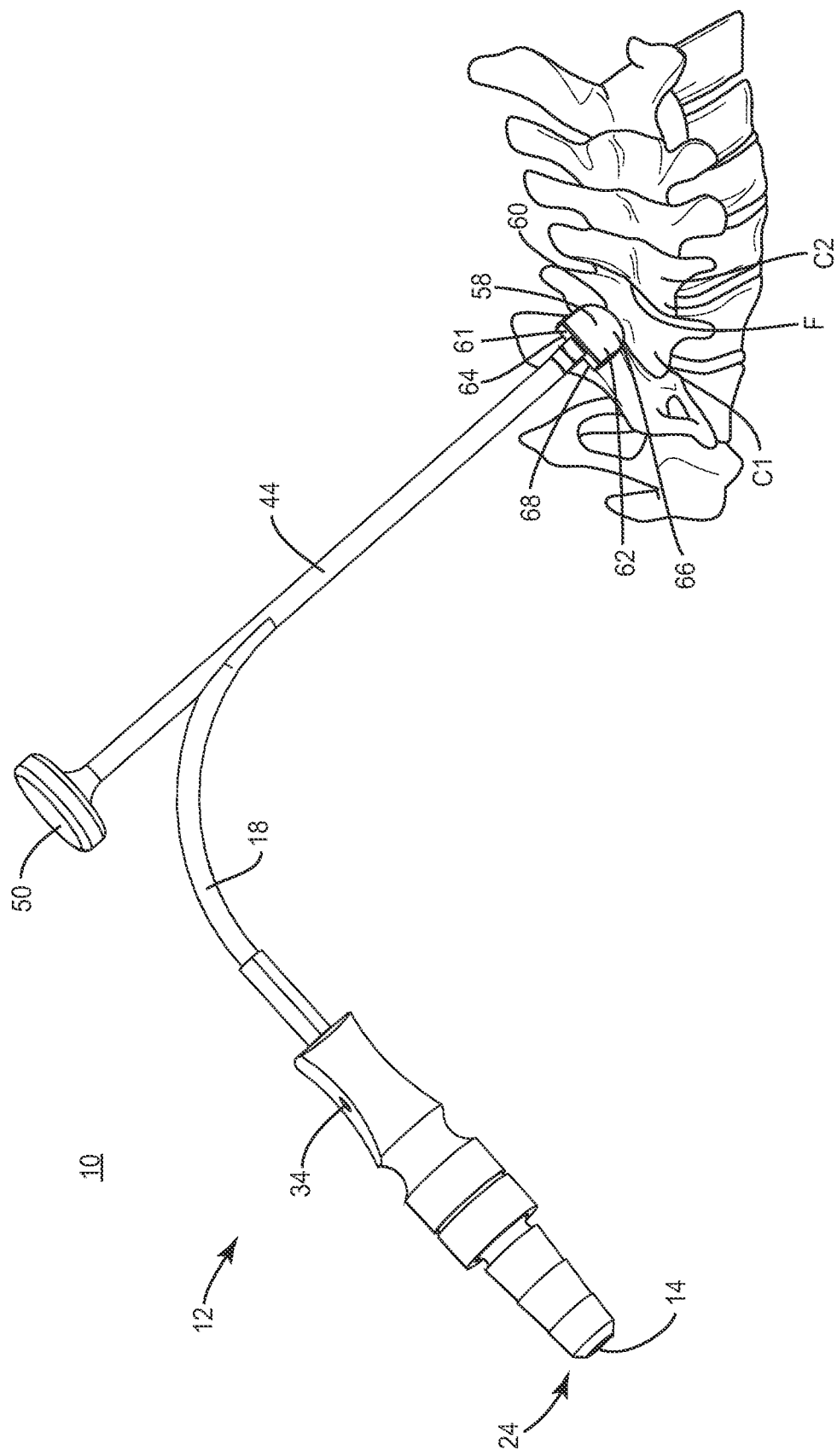
FIG. 5 is a perspective view of one embodiment of a system in accordance with the principles of the present disclosure disposed with cervical vertebrae.
Figure 6:
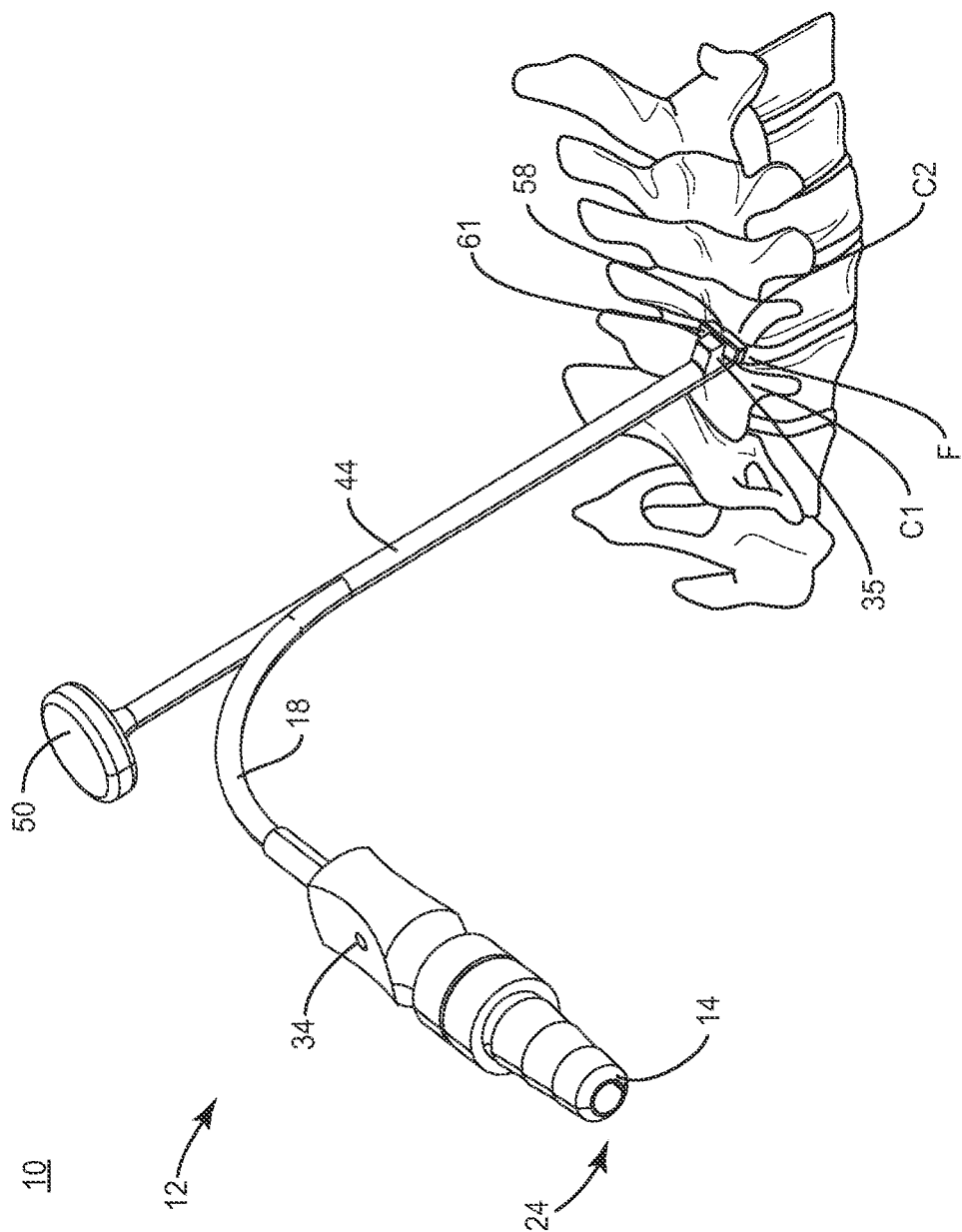
FIG. 6 is a perspective view of the system and cervical vertebrae shown in FIG. 5.

In one embodiment, as shown in FIGS. 5-6, spinal implant delivery system 10 includes an implant, such as, for example, a facet shim 58. Shim 58 is configured for engagement with face 38 (FIG. 2). Shim 58 includes a first lateral portion 60, which comprises an arcuate surface having a substantially even and/or uniform face, and side surfaces, extending from the arcuate surface, that have a substantially planar and/or uniform face. Shim 58 includes a second lateral portion 61, which has a substantially planar and/or uniform face. Portions 60, 61 extend about the perimeter of shim 58. Shim 58 includes a first side 62 and a second side 64. Portion 61 and side 64 are configured for engagement with surface 35, including opening 42. Opening 42 communicates with cavity 24 and is configured to provide a fluid and/or suction to draw shim 58 into engagement with surface 35, as described herein. It is contemplated that other portions and/or surfaces of shim 58 may be configured for engagement with surface 35.

In one embodiment, sides 62, 64 include grooved outer surfaces 66 and 68 respectively. It is contemplated that sides 62, 64 provide for enhanced fixation tissue adjacent cervical vertebrae C1, C2, as shown in FIGS. 5 and 6. It is further contemplated that sides 62, 64 may have alternate surface configurations, such as, for example, rough, arcuate, undulating, porous, semi-porous, dimpled, polished and/or textured according to the requirements of a particular application.

In operation, spinal implant delivery system 10, similar to that described above, is used to deliver shim 58 to a surgical site. Portion 61 of shim 58 is positioned at end 16 (FIG. 1) to engage surface 35 of delivery device 12. Suction source 26 is connected to end 20, as described, to enable vacuum for drawing fluid through conduit 18. Concave portions 31 of surface 30 are engaged with finger surface(s) of a medical practitioner, to seal cavity 24 to enable vacuum and to create suction through cavity 24. Fluid is drawn through conduit 18 such that suction flows through cavity 24 extending to opening 42. The fluid suction draws portion 61 and/or side 64 into engagement with surface 35 so that portion 61 and/or side 64 are releasably fixed with surface 35, as shown in FIG. 5. With portion 61 and/or side 64 fixed with surface 35, device 12 is introduced to the surgical site via the passageway to deliver shim 58 to the surgical site.

Upon delivery of shim 58 to the surgical site, portion 61 and/or side 64 maintain engagement with surface 35, as shown in FIG. 6. A force is applied to impact surface 50 via a surgical mallet, which translates along shaft 44 to impact face 56. Impact face 56 engages and applies the force to portion 61 and/or side 64 to position shim 58 within cervical facet joint space F, according to the requirements of a particular application.

The finger surface(s) are disengaged from opening 32 so that passageway 34 opens cavity 24. Vacuum is disabled such that suction is relieved from cavity 24, as described. Portion 61 and/or side 64 are released from surface 35 and shim 58 is implanted with cervical facet joint space F. Once shim 58 is released, device 12 is removed from the surgical site and the incision is closed.

In one embodiment, delivery device 12, similar to that described, includes surface 35 (FIG. 2), which engages a surface of one or a plurality of a cage, a spinal rod, a connector and/or a bone fastener, such as, for example, mono-axial screws and multi-axial screws for delivery of the same to a surgical site, similar to that described. For example, surface 35 can engage and hold screws to a driver instrument. This configuration facilitates rapid loading of the screws onto a driver instrument and avoids screws inadvertently and/or undesirably disengaging from the driver instrument, and/or undesirably failing to disengage from the driver instrument.

In one embodiment, as shown in FIGS. 7-8, spinal implant delivery system 100, similar to the apparatus and methods described above with regard to FIGS. 1-4, includes an implant delivery device 112. Device 112 is configured for engagement with an implant and a suction source, to deliver the implant to a surgical site, similar to that described. Device 112 extends between a proximal end 114 and a distal end 116. Device 112 includes a tubular conduit 118. Conduit 118 extends between a first end 120 and a second end 122. Conduit 118 defines a cavity 124 that extends between ends 120, 122. Conduit 118 includes an opening 125 at end 120. Opening 125 is disposed in communication with cavity 124.

Conduit 118 is configured to draw a fluid, via connection to the suction source, through cavity 124, similar to cavity 24 described above. Conduit 118 includes a linear portion 121 defining an axis aa extending from end 120 and an arcuate portion 119. Conduit 118 has a diameter D1. Diameter D1 is uniform. It is contemplated that conduit 118 may have various cross-section configurations, such as, for example, oval, rectangular, polygonal, irregular, tapered, offset, staggered, uniform and non-uniform. It is envisioned that one or all of the surfaces of conduit 118 may have alternate surface configurations, such as, for example, rough, threaded for connection with surgical instruments, arcuate, undulating, porous, semi-porous, dimpled, polished and/or textured according to the requirements of a particular application.

A suction source 126 is attached to end 120 of conduit 118. Source 126 includes flexible tubing and/or a cannulated instrument configured to draw fluid therethrough. The tubing is releasably connected to end 120. End 120 includes a luer connector port 123 adapted for a sealed connection with the tubing of source 126. It is envisioned that end 120 may be releasably connected, attached or monolithically formed with source 126. It is further envisioned that port 123 may alternatively include a threaded connection or quick disconnect coupling.

Source 126 is a source of vacuum configured to draw the fluid through cavity 124 similar to that described with regard to FIGS. 1-4. Source 126 includes a pump or other gas exhausting device to create vacuum.

End 120 includes a valve 127. Valve 127 is configured to selectively regulate the amount of fluid suction flowing through conduit 118 along cavity 124. Valve 127 includes a valve body 128. Body 128 includes an outer surface 130. Surface 130 defines a centrally disposed opening 132. Opening 132 communicates with a passageway 134 disposed in communication with cavity 124. Surface 130 includes concave portions 131, disposed on sides of body 128 and oriented in opposing directions, configured for engagement with a valve part (not shown). The valve part is engageable with portions 131 to selectively regulate suction and the drawing of fluid through conduit 118. Portions 131 are configured to receive the valve part, such as, for example, finger surface(s) of a medical practitioner. The finger surface(s) engage opening 132 to close and/or seal passageway 134 to enable the vacuum such that suction is provided to cavity 124 for drawing fluid through conduit 118. The finger surface(s) disengage from opening 132 to disable vacuum such that suction is relieved from cavity 124 and fluid is not drawn through conduit 118. In one embodiment, body 128 has a single opening 132. In one embodiment, portions 131 are planar. It is envisioned that the valve part may alternatively be a mechanical plug, hinge plug, tethered plug, dial regulated blockage and/or motorized valve component.

End 116 includes an implant engaging surface 135. It is contemplated that all or a portion of surface 135 may have alternate surface configurations according to the requirements of a particular application. Surface 135 includes a face 138, as shown in FIG. 8. Face 138 is configured for engagement with an implant (not shown) and defines an opening 142.

Opening 142 communicates with cavity 124 and is configured to provide a fluid and/or suction to draw an implant into engagement with 135.

Conduit 118 is connected with an impact shaft 144. Shaft 144 extends between a first end 146 and a second end 148. Shaft 144 defines a transverse axis bb extending between ends 146, 148, as shown in FIG. 7. Axis bb of shaft 144 extends transversely relative to end 122 of conduit 118. Shaft 144 merges with conduit 118 adjacent ends 148, 122. In one embodiment, shaft 144 merges with end 122 of conduit 118 at a 45-degree angle relative to axis bb. Shaft 144 is not in communication with cavity 124.

Shaft 144 has a solid configuration and has a diameter D2. Diameter D2 is uniform. It is contemplated that shaft 144 may have various cross-section configurations, for example, oval, rectangular, polygonal, irregular, tapered, offset, staggered, uniform and non-uniform. It is envisioned that one or all of the surfaces of shaft 144 may have alternate surface configurations, such as, for example, rough, threaded for connection with surgical instruments, arcuate, undulating, porous, semi-porous, dimpled, polished and/or textured according to the requirements of a particular application.

End 146 includes an impact surface 150. Surface 150 is circular. It is contemplated that surface 150 may be alternately configured, such as, for example, round, square, rectangular, polygonal or oval. It is contemplated that surface 150 may be smooth, rough, polished or textured according to the requirements of a particular application. Surface 150 includes a planar face 152. Face 152 is configured for engagement with a medical instrument. Surface 150 has a thickness, such as, for example, thickness T1. It is contemplated that the thickness of surface 150 may vary according to the requirements of a particular application.

End 148 includes an impact face 156, which comprises a portion of implant engaging surface 135, as shown in FIG. 8. Face 156 is disposed at an angular orientation, such as, for example, perpendicular, relative to face 138. Face 156 is configured for engagement with implant 140 to facilitate delivery and positioning of an implant at a surgical site, similar to that described with regard to FIGS. 1-4.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant delivery device comprising:
   a first wall defining a cavity disposed for communication with a suction source and extending between a first end and a second end, the first end including at least a portion of a valve disposed for communication with the cavity, the valve defining an opening including a passageway disposed in communication with the cavity, the second end including at least a portion of an implant engaging surface; and
   a second wall connected to the first wall and extending between a first end and a second end, the first end including an impact surface and the second end including at least a portion of the implant engaging surface,
   wherein the first end of the first wall includes a luer connector port that defines an opening disposed for communication with the cavity and the first wall has a linear portion, the valve and the opening in the luer connector port being coaxial with the linear portion.

2. A device as recited in claim 1, wherein the first wall is tubular and configured to draw a fluid through the cavity.

3. A device as recited in claim 1, wherein the suction source is connected to the first end of the first wall to draw a fluid through the cavity.

4. A device as recited in claim 1, wherein the valve includes an outer surface having a concave surface that includes the opening.

5. A device as recited in claim 1, wherein the first wall and the second wall merge adjacent the implant engaging surface.

6. A device as recited in claim 1, wherein the first wall has a first uniform diameter portion and the second wall has a second uniform diameter portion that merge into a third uniform diameter portion adjacent the implant engaging surface.

7. A device as recited in claim 1, wherein the second wall includes a solid configuration.

8. A device as recited in claim 1, wherein the second wall defines a longitudinal axis and the first wall extends transversely therefrom.

9. A device as recited in claim 1, wherein the impact surface includes a planar face.

10. A device as recited in claim 1, wherein the impact surface has a circular configuration defining a thickness and including a planar face.

11. A device as recited in claim 1, wherein the implant engaging surface defines an opening disposed for communication with the cavity.

12. A device as recited in claim 1, wherein the implant engaging surface includes an impact face.

13. A device as recited in claim 1, wherein the implant engaging surface includes a first face defining an opening and a second impact face disposed at an angular orientation relative to the first face.

14. A device as recited in claim 1, wherein the implant engaging surface includes a first face defining an opening and a second impact face disposed at a perpendicular orientation relative to the first face.

15. A device as recited in claim 1, wherein the implant engaging surface defines an opening disposed for communication with the cavity and the second wall extends along a longitudinal axis between the first and second ends of the second wall, the opening in the implant engaging surface being coaxial with the longitudinal axis.

16. A device as recited in claim 1, wherein the implant engaging surface includes a first face defining an opening and a second impact face disposed at a transverse orientation relative to the first face, the implant engaging surface including a planar surface opposite the second impact face, the second wall extending transversely from the planar surface.

17. A device as recited in claim 1, wherein the opening is disposed for engagement with a valve part that is detachable from the implant delivery device and configured to open and close the passageway.

18. A method for delivering an implant to a surgical site, the method comprising the steps of:
   providing the implant delivery device recited in claim 1;
   providing an implant;
   engaging the opening with a valve part that is detachable from the implant delivery device to close the cavity;
   applying suction to the cavity to draw fluid through the cavity such that the implant is drawn into engagement with the implant engaging surface;
   delivering the implant to the surgical site;
   engaging the impact surface such that the implant engaging surface selectively positions the implant at the surgical site; and
   disengaging the valve part from the opening to release the implant from the implant engaging surface at the surgical site.

19. A method as recited in claim 18, wherein the valve part is a finger surface of a medical practitioner.

20. An implant delivery system comprising:
a tubular conduit including an inner surface defining a first passageway and extending between a first end including at least a portion of a valve and a second end, the first end including a luer connector port that defines an opening disposed for communication with the first passageway, the first end including a linear portion, the valve and the opening being coaxial with the linear portion, the valve including a valve body having an outer surface including a concave surface defining a centrally disposed opening, the opening including a second passageway disposed in communication with the first passageway, the second end including at least a portion of an end surface defining a distal opening;
a suction source communicating with the first passageway;
an impact shaft defining a longitudinal axis and being connected with the conduit such that the conduit extends transversely therefrom, the shaft including a first end having a circular configuration defining a thickness and including a planar impact surface, the shaft including a second end including at least a portion of the end surface defining an impact face; and
an implant,
wherein the opening of the valve body is disposed for engagement with a valve part that is configured to close the second passageway such that the suction source draws a gas through the first passageway to draw the implant into engagement with the distal opening and the valve part is disengageable from the opening to open the second passageway such that the implant is released from the distal opening.

* * * * *